US012226649B2

(12) United States Patent
 Kosecoff

(10) Patent No.: US 12,226,649 B2
(45) Date of Patent: Feb. 18, 2025

(54) SKIN CONTOURING USING PHOTO-RESPONSIVE MATERIALS

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/324,581

(22) Filed: May 19, 2021

(65) Prior Publication Data

US 2022/0370822 A1     Nov. 24, 2022

(51) Int. Cl.
  *A61N 5/06*  (2006.01)
  *A61K 8/04*  (2006.01)
  *G06T 7/73*  (2017.01)

(52) U.S. Cl.
  CPC ............ *A61N 5/0616* (2013.01); *A61K 8/042* (2013.01); *G06T 7/73* (2017.01);
  (Continued)

(58) Field of Classification Search
  CPC .......... A61N 5/0616; A61N 2005/0635; A61N 2005/0658; G06T 7/73; G06T 2207/3008; A61K 8/042
  See application file for complete search history.

(56) References Cited

U.S. PATENT DOCUMENTS

| 8,562,657 B2 | 10/2013 | Ferren et al. |
| 2003/0170308 A1* | 9/2003 | Cleary ...................... A61K 8/73 424/487 |

(Continued)

FOREIGN PATENT DOCUMENTS

| CN | 112273839 A | 1/2021 |
| EP | 3586926 A1 | 1/2020 |

(Continued)

OTHER PUBLICATIONS

Lee, J. H., Roh, M. R., & Lee, K. H. (2006). Effects of infrared radiation on skin photo-aging and pigmentation. Yonsei Medical Journal, 47(4), 485. https://doi.org/10.3349/ymj.2006.47.4.485 (Year: 2006).*

(Continued)

*Primary Examiner* — Gary Jackson
*Assistant Examiner* — Skylar Lindsey Christianson
(74) *Attorney, Agent, or Firm* — Christensen O'Connor Johnson Kindness PLLC

(57) ABSTRACT

Methods, systems, and devices for integrated photo-responsive contouring treatment are described. Methods include identifying a region of skin corresponding to a contouring treatment of the skin. The region of skin may be provided with a photo-responsive material overlying a portion of the region of the skin. Methods may include identifying one or more treatment regions overlapping the photo-responsive material. The treatment regions may be identified at least in part to apply the contouring treatment. Methods may include determining an irradiation profile for each of the one or more treatment regions to contour each respective treatment region as part of applying the contouring treatment. Methods may also include irradiating the photo-responsive material at the one or more treatment regions in accordance with the respective irradiation profiles. Irradiating the photo-responsive material may induce a localized change in shape of the photo-responsive material in the respective treatment regions.

20 Claims, 8 Drawing Sheets

(52) U.S. Cl.
CPC ............... *A61N 2005/0635* (2013.01); *A61N 2005/0658* (2013.01); *G06T 2207/30088* (2013.01)

(56) References Cited

U.S. PATENT DOCUMENTS

| | | | |
|---|---|---|---|
| 2007/0038270 | A1* | 2/2007 | Ferren ............... A61N 5/062 607/88 |
| 2012/0024308 | A1 | 2/2012 | Giron et al. |
| 2016/0184212 | A1 | 6/2016 | Casasanta, III et al. |
| 2016/0331308 | A1* | 11/2016 | Zhou ............... A61M 35/003 |
| 2019/0030359 | A1 | 1/2019 | Dijkstra et al. |
| 2020/0375526 | A1 | 12/2020 | Oh et al. |
| 2021/0244204 | A1 | 8/2021 | Shin |

FOREIGN PATENT DOCUMENTS

| | | | |
|---|---|---|---|
| EP | 3632507 | A1 | 4/2020 |
| FR | 2988603 | A1 | 10/2013 |
| KR | 101900450 | B1 | 9/2018 |
| KR | 20200098926 | A | 8/2020 |
| KR | 102193581 | B1 | 12/2020 |
| WO | 2016041067 | A1 | 3/2016 |

OTHER PUBLICATIONS

Rebers et al., Differentiation of physical and chemical cross-linking in gelatin methacryloyl hydrogels, Scientific Reports, 2021.
Van Hoorick et al., (Photo-) croslinkable gelatin derivatives for biofabrication applications, Elsevier, 2019.
Yao et al., Photo Processing for Biomedical Hydrogels Design and Functionality: A Review, www.mdpi.com/journal/polymers, 2018.
International Preliminary Report on Patentability and Written Opinion of The International Searching Authority dated Nov. 21, 2023, issued in corresponding International Application No. PCT/US2022/029577, filed May 17, 2022, 9 pages.
International Search Report dated Sep. 6, 2022, issued in corresponding International Application No. PCT/US2022/029577, filed May 17, 2022, 4 pages.
Rapport De Recherche Préliminaire dated Oct. 5, 2023, issued in corresponding French Application No. 2107575, filed Sep. 2, 2021, 1 page.
Opinion Écrite Sur La Brevetabilité De L'Invention dated Oct. 5, 2023, issued in corresponding French Application No. 2107575, filed Sep. 2, 2021, 4 pages.

* cited by examiner

SKIN CONTOURING USING PHOTO-RESPONSIVE MATERIALS

SUMMARY

Methods, systems, and devices for integrated photo-responsive contouring treatment are described. In some embodiments, a method of contouring skin includes identifying a region of skin corresponding to a contouring treatment of the skin. The region of skin may be provided with a photo-responsive material overlying a portion of the region of the skin. The method may include identifying one or more treatment regions overlapping the photo-responsive material. The treatment regions may be identified at least in part to apply the contouring treatment. The method may include determining an irradiation profile for each of the one or more treatment regions to contour each respective treatment region as part of applying the contouring treatment. The method may also include irradiating the photo-responsive material at the one or more treatment regions in accordance with the respective irradiation profiles. Irradiating the photo-responsive material may induce a localized change in shape of the photo-responsive material in the respective treatment regions.

The region of skin may be coextensive with lines or wrinkles of the skin. The contouring treatment may include expanding or contracting the skin within or around the region of skin. The irradiation profile may define a volumetric pattern within the treatment region. The localized change in shape may define a contraction or an expansion of one or more outer layers of the first region of skin. The photo-responsive material may be characterized by a physical contraction in response to illumination at a characteristic wavelength. The photo-responsive material may be characterized by a physical expansion in response to illumination at a characteristic wavelength. The photo-responsive material may include two constituent materials. The photo-responsive material may expand in response to exposure at a first characteristic wavelength. The photo-responsive material may contract in response to exposure at a second characteristic wavelength. The photo-responsive material may be or include a hydrogel monomer that forms a cross-linked hydrogel when under illumination at a characteristic wavelength. The hydrogel monomer may be or include gelatin methacryloyl (Gel-MA), hydroxyethylmethacrylate (HEMA), or ethylene glycol diacrylate (EGDA). The irradiation profile for a treatment region of the one or more treatment regions may define a pattern. The pattern may induce an anisotropic contraction or an anisotropic expansion of the first region of skin.

Identifying the first region of skin may include capturing an image including the first region of skin using a camera and determining a feature of the skin. Determining the feature of the skin may include generating a 3D mapping of the skin and predicting a location and a type of the feature of the skin on the 3D map using a feature detection system configured to recognize the feature of the skin when provided with the 3D map of the skin. The method may further include receiving a numerical representation of a contouring treatment design and modifying the contouring treatment design to reflect the location and the type of the feature of the skin. The feature of the skin may include a wrinkle, a fine line, a scar, a blemish, or a region of loose skin.

In some embodiments, a non-transitory computer-readable memory stores instructions that, when executed by one or more processors of a computer system, cause the computer system to implement operations of the above method or its variations.

In some embodiments, systems for applying a contouring treatment to a target body surface include an illumination source, physically coupled to a visible light mirror having a first portion being at least partially transparent to visible light, the illumination source configured to emit one or more discrete electromagnetic stimuli of character and for a duration sufficient to induce a localized change in a photo-responsive material disposed on a surface of a biological subject, wherein each discrete electromagnetic stimulus has a discrete peak emission wavelength. The systems may include a camera, optically coupled with the visible light mirror to receive visible light via the first portion. The systems may also include a controller operably coupled to the illumination source and the camera and including computational circuitry configured to initiate irradiation of the photo-responsive material disposed on the surface of the biological subject in accordance with a respective irradiation profile so as to induce a localized change in shape or state of the photo-responsive material.

In some embodiments, a system includes means for determining irradiation profile for each of the one or more treatment regions to contour each respective treatment region as part of applying the contouring treatment. The system may also include means for creating structures on a surface of a biological subject by inducing a localized change in a photo-responsive material.

BRIEF DESCRIPTION OF THE FIGURES

The foregoing aspects and many of the attendant advantages of the present disclosure become will more readily appreciated as the same become better understood by reference to the following detailed description, when taken in conjunction with the accompanying drawings.

DETAILED DESCRIPTION

Figure 1:
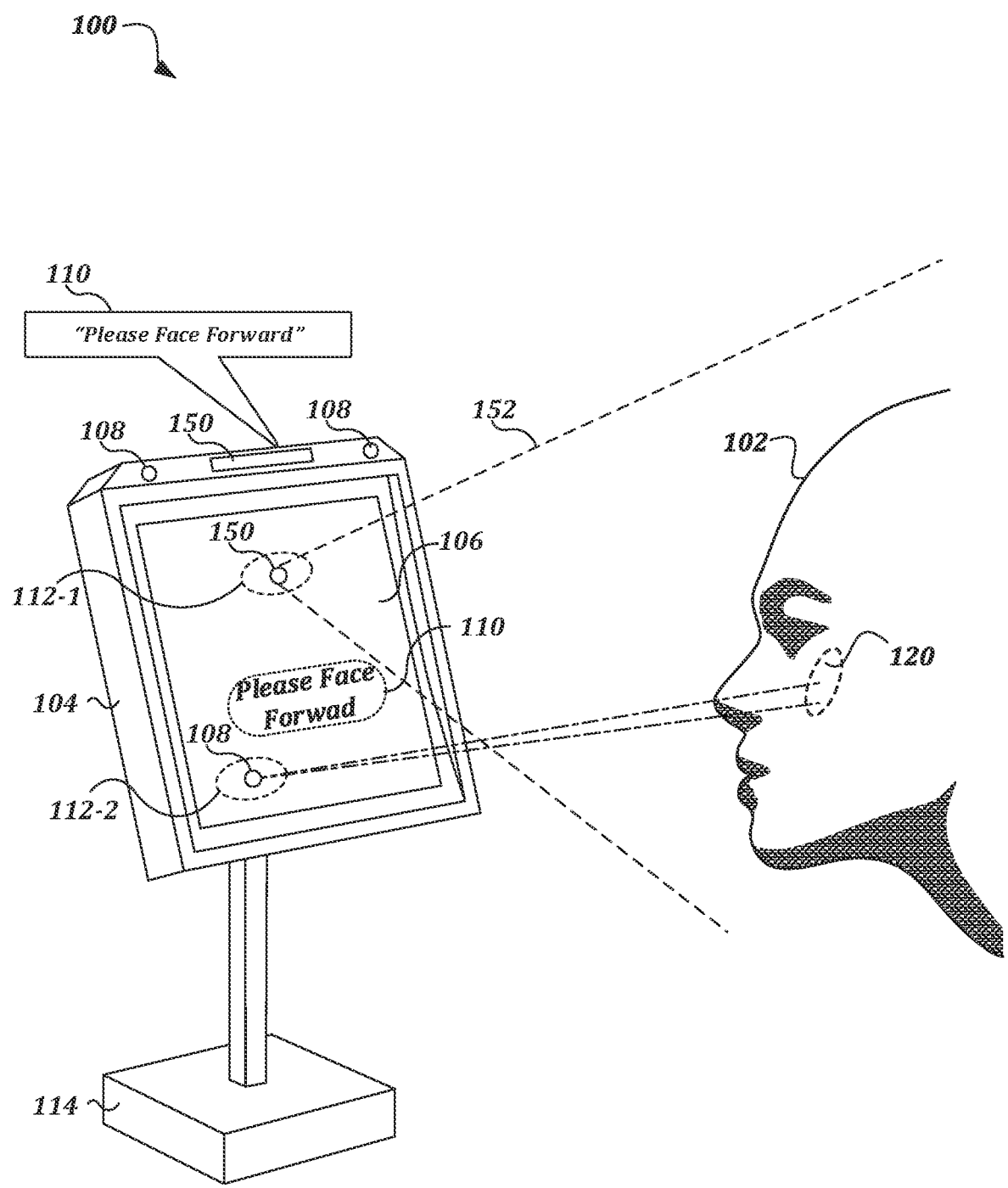
FIG. 1 is a schematic illustration of an embodiment of a system incorporating sensors and an illumination source for application of cosmetic designs, in accordance with various embodiments.

Application of cosmetics and makeup in patterns and shapes can be difficult by hand Many individuals use products or resort to surgeries to correct loose skin, sagging skin, lines, and wrinkles on regions of the face and body. For lifting or spreading the skin, skin is distributed to other locations or is removed by physical or chemical exfoliation. Where and how to direct the excess skin in a effective, aesthetically desirable way is a challenging, artistic act. In certain instances, cosmetic contouring treatments include both pushing apart (expanding) the skin and pulling in (contracting the skin) Currently, contouring solutions typically involve harsh chemical treatments, such as acid peels, surgical intervention, or sub-cutaneous injection of cytotoxic compounds.

Systems, methods, and photo-responsive materials are described for applying contouring treatments on a body surface, such as a subject's face or other region of interest, using one or more illumination sources. Described embodiments use photo-responsive materials exhibiting shape-change, contraction, or expansion to apply one or more contouring treatments mapped to the body surface using a projection of a cosmetic treatment design onto a 3D mapping of the body surface. Described embodiments are useful in many contexts, including cosmetics or body art applications, skin feature mapping or monitoring, dermatological diagnosis or treatments, or telehealth applications. In the context of such applications, described embodiments provide precision and greater ease of use over complex manual routines and improve accessibility of at-home cosmetic treatment without a clinic visit.

In described embodiments, a transparent skincare deposit can be used to keep the natural color of the skin, or on the contrary, an opaque pigmented make-up deposit can be used to homogeneously conceal skin imperfections with a change in color. Translucence can achieve no color change while diffusing the natural "background" colors. Digital light processing (DLP)-based bioprinting technologies can use Near Infrared (NIR) light to 3D photopolymerize a material (eg a hydrogel monomer), both in vivo and in vitro. If the material is properly translucent its polymerized state, it cyan be used to more seamlessly (less disruptively) fill gaps created by crater acne, wrinkles, and lip contours in terms of color distribution. By controlling the 3D shape of the deposit and matching its contours with the surrounding surfaces, the material can be even more seamlessly (less disruptively) integrated, avoiding excess fill (bumps) or underfill (recesses).

In described embodiments, a biocompatible hydrogel monomer or other polymer precursor can be applied to the body surface and/or absorbed sub-cutaneously. The material might have properties such that when cured it will physically contract and/or expand, creating a tighter bond between various anchored coordinates. In this way, the skin can be temporarily tightened, lifted, or tucked without the use of surgical equipment or aggressive procedures and/or externally visible scaffolding. The biocompatible material can be photopolymerized or otherwise modified using exposure to one or more illumination sources to a desired shape across various depths on and through the skin, and may be actuated/modulated/addressed by one or more wavelengths, as part of applying the cosmetic treatment design to the body surface.

Without being limited to a specific system or method, systems and methods for applying such cosmetic designs are also described in the context of a sensor-bearing system. Sensors suitable for use in described embodiments include 2-dimensional (2D) or 3-dimensional (3D) cameras, proximity sensors, or other integrated or peripheral cameras or sensors. Depth sensors are used in some embodiments to obtain 3D information about surfaces and include a range of possible hardware suitable for this purpose, including RGB or infrared stereoscopic cameras, laser or infrared LiDAR sensors, and dot projectors. 3D scans enable improved measurement of actual dimensions of a body surface and allow depth sensing, which can help to determine, for example, how far the body surface is from the camera, or detailed information about particular skin features, such as wrinkles. Reference points obtained through high-quality 3D scanning in accordance with described embodiments provides greater accuracy for determining location than traditional reference points obtained with 2D imaging, such as eyes, lips, noses, or other prominent facial features, and are particularly helpful where the region of interest is occluded.

In some embodiments, systems for applying a contouring treatment to a target body surface include an illumination source, physically coupled to a visible light mirror having a first portion being at least partially transparent to visible light, the illumination source configured to emit one or more discrete electromagnetic stimuli of a character and for a duration sufficient to induce a localized change in a photo-responsive material disposed on a surface of a biological subject, wherein each discrete electromagnetic stimulus has a discrete peak emission wavelength. In this context, the term "discrete electromagnetic stimuli" is used in reference to energy emitted from a source, including, but not limited to, photons, radio waves, microwaves, x-rays, or ions. In the forthcoming paragraphs, description of discrete electromagnetic stimuli focuses on photons in the ultraviolet, visible, near infrared, and infrared ranges, produced by one or more illumination sources. In this context, the term "biological subject" is used in reference to a tissue or other surface associated with a living organism, including, but not limited to skin, hair, keratin (e.g., nails), or internal organ tissues of human or ion-human organisms. In the forthcoming paragraphs, description of biological subjects focuses on one or more target body surfaces, such as the face, hands, or other skin surfaces. In this context, the term "peak emission wavelength" is used in reference to an energy (e.g., as described in terms of wavelength, wavenumber, electron-volts, etc.) at which a local and/or global maximum in emission intensity is observed, which may be described by an emission intensity distribution as a function of energy. In the forthcoming paragraphs, peak emission wavelength refers to an example of a central wavelength, describing an illumination source from which the output emission distribution is centered or otherwise distributed around the peak emission wavelength.

The systems may include a camera, optically coupled with the visible light mirror to receive visible light via the first portion. The systems may also include a controller operably coupled to the illumination source and the camera and including computational circuitry configured to initiate irradiation of the photo-responsive material disposed on the surface of the biological subject in accordance with a respective irradiation profile so as to induce a localized change in shape or state of the photo-responsive material. In this context, the term "computational circuitry" is used in reference to operational components of a computer system, including but not limited to volatile and/or nonvolatile memory devices, data transmission subsystems (e.g., bus), and/or software and/or firmware provided to implement contouring treatments using photo-responsive materials. In this context, the term "controller" is used in reference to operational electronic components configured to control active components of systems described herein, in accordance with electronic instructions from the computer system (e.g., processor(s) and computational circuitry).

In some embodiments, systems are described in terms of a means for determining an irradiation profile for each of the one or more treatment regions to contour each respective treatment region as part of applying the contouring treatment. In this context, the term "means" is used in reference to the systems described in the forthcoming paragraphs, such as the computational circuitry described above as well as systems and components for defining surface mappings of biological subjects. The system may also include means for creating structures on a surface of a biological subject by inducing a localized change in a photo-responsive material. In this context the means may be understood to describe sources and control systems for generating discrete electromagnetic stimuli, such as illumination sources, directed toward a biological subject.

The systems described expose the surface with multiple actuating wavelengths in accordance with the treatment design as mapped onto the 3D information collected by the sensors. In this way, the photo-responsive material, applied to a region of the body surface, can be made to apply one or more contouring morphology changes as described by the cosmetic treatment design accurately and precisely by illumination with the actuating wavelengths rather than manual application of force to the skin. Advantageously, the materials, systems, and methods described also provide improved accessibility to users with limited mobility or dexterity, for whom cosmetic treatments, such as precise application of cosmetic creams, may otherwise involve assistance by another person.

FIG. 1 is a schematic illustration of an example system 100 incorporating sensors and an illumination source for application of cosmetic designs, according to various embodiments. While the embodiments of the photo-responsive material described in reference to the forthcoming figures are illustrated in the context of example system 100, alternative approaches are also contemplated. The system 100 is not intended as the sole system for use with the photo-responsive materials described below.

As part of the example system 100, one or more cameras 150 of a client computing device 104 includes one or more cameras and captures images of a subject's face 102. In the example shown, the client computing device 104 is a purpose-built mobile computing device including a visible light mirror 106, one or more illumination sources 108, and one or more user interface elements 110 to prompt the subject with visual and/or auditory prompts. For example, the interface elements 110 may be or include a display electronically coupled with the computer system to generate a visual prompt (e.g., "please face forward") either in a peripheral physically coupled with the mirror 106. Additionally or alternatively, the client computing device 104 may be electronically coupled with an acoustic speaker to generate an auditory prompt.

The mirror 106 may include one or more portions 112 characterized by unidirectional transparency, for example, in ultraviolet, visible, and/or infrared spectral ranges. The camera(s) 150 may be optically coupled with the visible light mirror 106 to receive visible light via a first portion 112-1, and the illumination sources) 108 may be optically coupled with the visible light mirror 106 and configured to emit a plurality of discrete wavelength channels via a second portion 112-2 of the mirror 106. In this way, the mirror 106 may appear uniform, and the system 100 may appear aesthetically as an ordinary cosmetic mirror without outward indication that the system 100 incorporates electronics, cameras 150, or illumination sources 108. For example, the components of the client computing device 104 may be integrated into a housing 114 that appears similar to a consumer cosmetic mirror rather than an electronics system. In this example, the housing 114 may conceal power sources, heat management systems, and other components.

While the client computing device 104 is illustrated in a particular configuration (e.g., as a countertop mirror or vanity mirror), additional and/or alternative form factors are contemplated. For example, the system 100 may include a smartphone or tablet computer in communication with the client computing device 104, such that one or more computer-executable operations are undertaken by the smartphone or tablet computer rather than by the client computing device 104. In this way, the client computing device 104 may be or include smaller housings 114, including, but not limited to, a cosmetics compact or an electronic peripheral configured to electronically couple with a smartphone or tablet computer that includes the camera 150, the illumination source 108, or both. Similarly, the mirror 106 can be or include a full-size wall mirror, such that the client computing device 104, the camera(s) 150 and the illumination source(s) 108 may be positioned behind the mirror 106 and the one or more portions 112 may be located relative to the camera(s) 150 and the illumination source(s) 108. It such a configuration, the system 100 may be installed as a fixture rather than as a portable system and a single mirror 106 may be configured to conceal multiple client computing devices 104, multiple cameras 150, and multiple illumination sources 108, corresponding to a number of "treatment stations," as in an aesthetic clinic.

The illumination source 108 may include one or more optics configured to form a beam and to scan the beam. The optics may include lenses or mirrors internal to the housing 114 that may be actuated or otherwise controlled to direct a beat from the illumination source(s) 108 to the subject's face 102. For example, the illumination source 108 may be or include one or more laser sources corresponding to the plurality of discrete wavelength channels. In some embodiments, the illumination source 108 includes multiple light-emitting diodes corresponding to the plurality of discrete wavelength channels. Similarly, the illumination source may be or include a continuous source (e.g., a tungsten halide or broad-spectrum source) and a plurality of bandpass filters to generate the discrete wavelength channels used by the system 100 to apply a cosmetic design. Addressable arrays of illumination data, described in more detail in reference to FIG. 2A and FIG. 2B, may be implemented by DLP techniques.

The client computing device 104 may be in electronic communication with additional systems via a network or over near-field communication protocols (e.g., wifi, bluetooth, etc.). For example, the client computing device 104 may pair with a mobile electronic device, such as a smart phone or tablet, from which the client computing device 104 may receive an identifier of a treatment design. Similarly, the client computing device 104 may communicate with a server, storing numerical representations of designs, and may access the design from the server. The server may be a remote server or may be a local server, where the terms "remote" and "local" are used both to refer to physical proximity to the system 100 and to denote whether the client computing device 104 and the server are configured to communicate over a public network, such as the internet, or a distributed network system (e.g., a cloud system). In some cases, the client computing device 104 may store design data locally for a number of cosmetic designs, for example, using a non transitory computer readable storage medium (e.g., SSD flash memory, hard disk drives, etc.). For example, the client computing device 104 may receive newly released cosmetic treatment design data and associated metadata from the server, such as identifier information and interface data (e.g., images representing the cosmetic design on a model), which may be provided via the interface elements 110 or via the mobile electronic device. In such cases, the system may be configured to operate with intermittent or no network connectivity.

In some embodiments, the camera 150 acts as a far-field camera positioned and configured to capture video or still images of subject's face 102, as yell a region of interest 120 of the subject's face 102, such that the region of interest 120 is within the field of view 152 of the camera(s) 150. In the example shown, the region of interest 120 is shown as a portion of the left cheek of the subject's face 102, but the region of interest 120 may cover a larger portion of the subject's face 102, such as the entirety of the subject's face 102. In some embodiments, the camera unit 150 includes more than one camera, such as for stereoscopic image or video capture and/or depth sensing. In some embodiments, the camera unit 150 also includes one or ore sensors other than cameras (e.g., a LiDAR sensor or infrared dot projector for depth sensing, a proximity sensor for proximity detection, etc.). In some embodiments, an infrared dot projector projects infrared dots onto a surface, and reflections from the surface are measured by an infrared camera to determine the distance each dot is from the projector system. When working in conjunction with a 3D camera, these depth measurements can be mapped onto a captured 3D image. This approach is used in some embodiments to generate a 3D model of a body surface, and for real-time tracking of additional features to be used for mapping a cosmetic treatment design onto the subject's face 102 or other body parts.

Figure 2A:
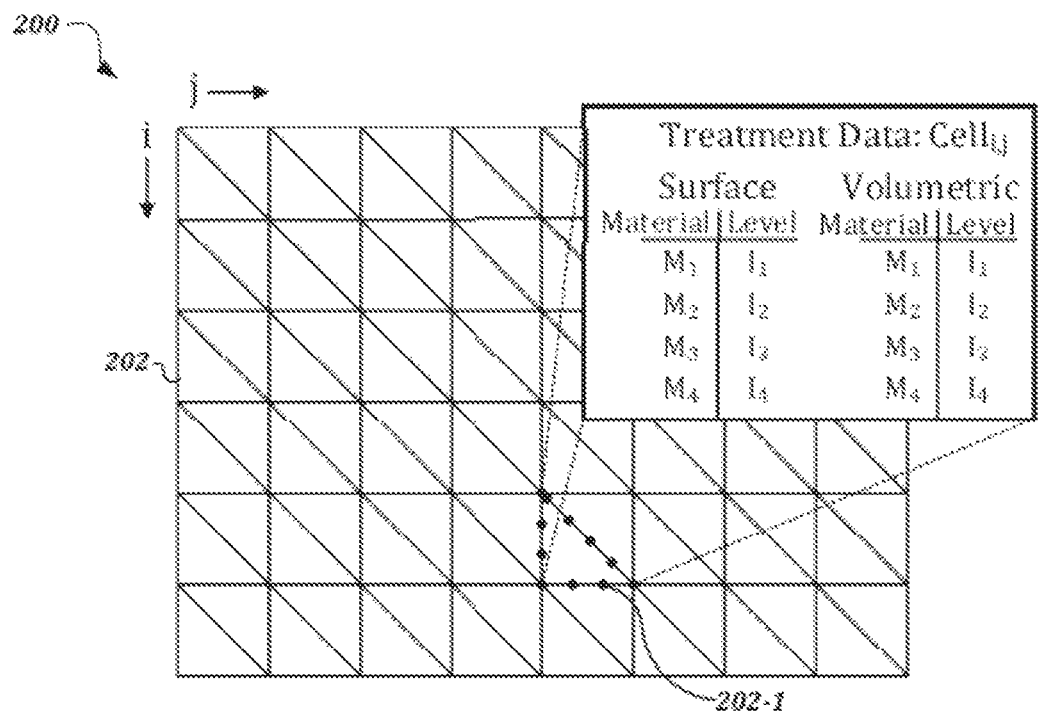
FIG. 2A is a schematic illustration of a numerical representation of a contouring treatment as a polygonal mesh including a tensor of treatment data in a face-on direction and a low-angle direction, in accordance with various embodiments.

FIG. 2A is a schematic illustration of a numerical representation of a contouring treatment 200 as a polygonal mesh including a tensor of treatment data for surface and volumetric treatments, in accordance with various embodiments. The treatment design 200 represents an exemplary visualization of a cosmetic treatment design, including multiple polygons 202, where each polygon 202 represents a unit of the numerical representation, akin to a pixel in a digital image. Where the system implementing the processes described herein (e.g., system 100 of FIG. 1) may project the design 200 onto a surface mapping of a user's face (e.g., subject's face 102 of FIG. 1), the polygons 202 may be or include triangles or other shapes that provide greater flexibility for projection and surface mapping relative to square or rectangular pixels.

As shown, a first polygon 202-1 of the treatment design 200, referenced as $Cell_{i,j}$ in the i-j plane of the numerical representation, may include multiple types of treatment data corresponding to different layers of the cosmetic treatment design 200. For example, the design data for the first polygon 202-1 may include, but is not limited to, a surface treatment tuple and a volumetric treatment tuple, indicating two different treatments to be generated by the system 100 at different regions of the skin. Each tuple may include treatment level information corresponding to the photo-responsive materials incorporated into a photo-responsive formulation. For example, the photo-responsive formulation may include one, two, three, four, five, or more different photo-responsive materials. In some embodiments, one or more of the materials may expand under illumination at a characteristic wavelength, while others may contract, harden, or change color in response to illumination at a respective characteristic wavelength.

By selectively modulating the photo-responsive materials in accordance with the treatment levels for each polygon, the treatment design 200 may be applied a target body surface of the user. As described in more detail in reference to FIG. 3-FIG. 6B, treatments may be designed to provide isotropic and/or anisotropic contouring on the surface of a user's skin, as a volumetric contouring treatment, and/or to reduce the visual appearance of skin features including, but not limited to, acne, acne scars, scars, wrinkles, or lines. While each polygon 202 is illustrated as having a uniform characteristic size, it is to be understood that the polygons are representative of a tensor of contouring information that is referenced by cell entries in i-j space, rather than in cartesian coordinates. In this way, the first polygon 202-1 may be larger or smaller than neighboring polygons 202 when projected into a physical dimension, such as when applied to a facial mapping of a user for application of the design 200 (e.g., region of interest 120 of the subject's face 102 of FIG. 1).

Figure 2B:
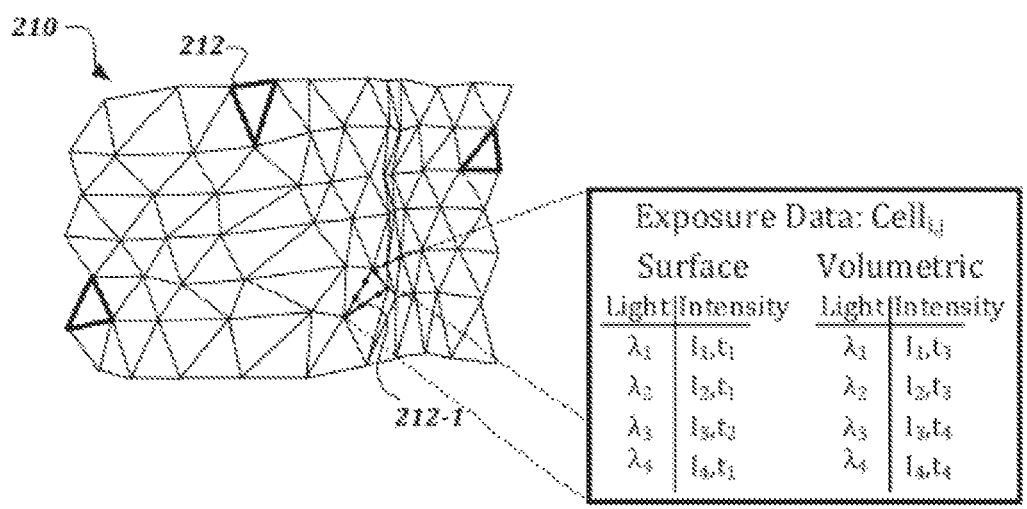
FIG. 2B is a schematic illustration of a 3-dimensional model projection of the contouring treatment onto a face mapping, in accordance with various embodiments.

FIG. 2B is a schematic illustration of an example 3-dimensional projection 210 of the treatment design 200 onto a face mapping collected using the system of FIG. 1, according to various embodiments. As described in more detail in reference to FIG. 1, the system 100 is configured to receive the treatment design 200 and to generate an exposure pattern. As part of the operations of the system 100, the treatment design 200 may be projected onto a 3D mapping of the portion of the user's body (e.g., subject's face 102 of FIG. 1), The 3D model includes several reference points 212 in the form of corresponding triangles of a mesh structure, although other polygon shapes are also contemplated.

Generating the 3D projection 210 may include multiple computational operations to generate a numerical representation of a portion of a face of the user using the camera (e.g., a facial mapping). The camera may be or include multiple image sensors configured to capture stereoscopic images. In this way, the numerical representation of the portion of the face may be or include a tensor of position information defining a surface of the target body surface (e.g., in the region of interest 120 of FIG. 1). Examples of computational techniques include edge-detection, feature or point detection and tracking, and/or point-cloud methods. For example, the system 100 may be configured with a time-of-flight camera, with LiDAR systems, or with stereoscopic cameras, such that the facial mapping may represent a surface generated by contours connecting points and/or features. In some embodiments, the system 100 may include an implementation of machine learning, such as a face detection/mapping module that may be trained to predict the facial mapping based on a subset of features and/or points measured by the camera. In this way, the system 100 may be configured to reduce the number of measurements used to generate the mapping, which may improve system performance, for example, by reducing the length of time used to capture images of the user's face.

Other adaptations can be performed for variations in lighting conditions, viewing angles, or other factors. As one example, a light sensor mounted on the client computing device 104 can be used to measure current lighting conditions relative to a baseline lighting condition. If the environment is too bright or too dark, the client computing device 104 may generate a prompt to increase illumination and/or may activate an illumination source (e.g., illumination source 108 of FIG. 1) that may or may not be visible to the subject (e.g., an infrared source to provide invisible illumination). In some embodiments, the client computing device 104 may provide feedback to a user (e.g., via synthesized voice cues or visual indications) to adjust the lighting conditions for better results. In some embodiments, the system may generate feedback to instruct the user to reposition relative to the camera(s) (e.g., generating a prompt to reposition the user's face from a face-on to a side-on position). It should be understood that described embodiments are capable of implementation in many possible ways to determine matches between captured image data and texture data in a 3D model, including matching detected edges or contours, color/pixel values, depth information, or the like in different combinations, and at particular threshold levels of confidence, any of which may be adjusted based on lighting conditions, user preferences, system design constraints, or other factors.

The projection 210 may be generated by various means to reduce artifacts of the projection onto the face. For example, the polygons into which the design 200 is divided may be heterogeneously scaled, skewed, or otherwise modified when generating the projection 210, as illustrated. For example, where the treatment design 200 may include each polygon with a uniform size, the projection 210 may include many different sizes for the polygons 212. In some embodiments, resizing may correspond to the contours of the facial mapping, where regions of high dynamic range correspond to smaller polygons 212 and regions of low dynamic range correspond to larger polygons 212. Additionally and/or alternatively, the projection 210 may be resized in accordance with information density. For example, where the number of polygons 202 making up the treatment design 200 correspond to the resolution of the design, analogous to a pixel resolution of a digital image, information-dense regions of the design 200 may include relatively high numbers of polygons 202, compared to regions that include relatively sparse design information. As an illustrative example, more polygons may be used to describe the regions around facial features, such as eyes, nose, mouth, or eyebrows, in contrast to regions of the cheeks, jaw, forehead, etc.

The exposure data illustrated in FIG. 2B may be generated by taking into account the intensity values of each material channel included in the design 200, as well as exposure kinetics data for the photo-responsive materials. For example, treatment values for a first polygon 212-1, as indicated by the intensity data of the design 200, may be effected by exposing the first polygon to the multiple distinct wavelength channels (e.g., $\lambda_{1-4}$) for different durations corresponding to the characteristic chemical kinetics of the different materials. In some embodiments, a "wipe" operation may be implemented by exposing the photo-responsive materials to a neutralization or breakdown-wavelength. In some embodiments, photo-responsive materials undergo irreversible polymerization, isomerization, or shape-change transformations under illumination at one or more of the distinct wavelength channels. Through use of biocompatible and non-toxic photo-responsive materials, the cosmetic treatment may be temporary, with little to no deleterious effect on the skin.

In some embodiments, the treatment design 200 may be adapted using data collected during facial mapping operations to determine cosmetic treatments targeting one or more regions of skin of the user (e.g., region of interest 120 of FIG. 1). In this way, using depth information, edges, and/or other features, the treatment design 200 may incorporate specific features and configurations of illumination. In an illustrative example, a template treatment design may be received by the system implementing contouring treatments, and may be adjusted to include treatment information addressing loose skin or wrinkles, and/or acne scars, detected during face mapping. As such, the projection of the treatment design 200 onto the face mapping 210 may include adaptive mesh sizing and treatment levels, corresponding to identification of features and/or treatment regions. In some embodiments, the features and/or treatment regions may be manually indicated, for example, by using a visibly-transparent fluorescent marker or other indicator that can be detected by optical sensors (e.g., UV absorbing ink, IR absorbing ink, etc), which can be used to indicate a specific treatment location, for example, by associating a specific indicator with a specific treatment. In an illustrative example, a UV-visible-NIR-IR image sensor system (e.g., camera(s) 150 of FIG. 1) can be used to detect two or more types of indicators for surface treatments, where a first indicator is associated with expansion treatment and a second indicator is associated with contraction treatment.

Figure 3:
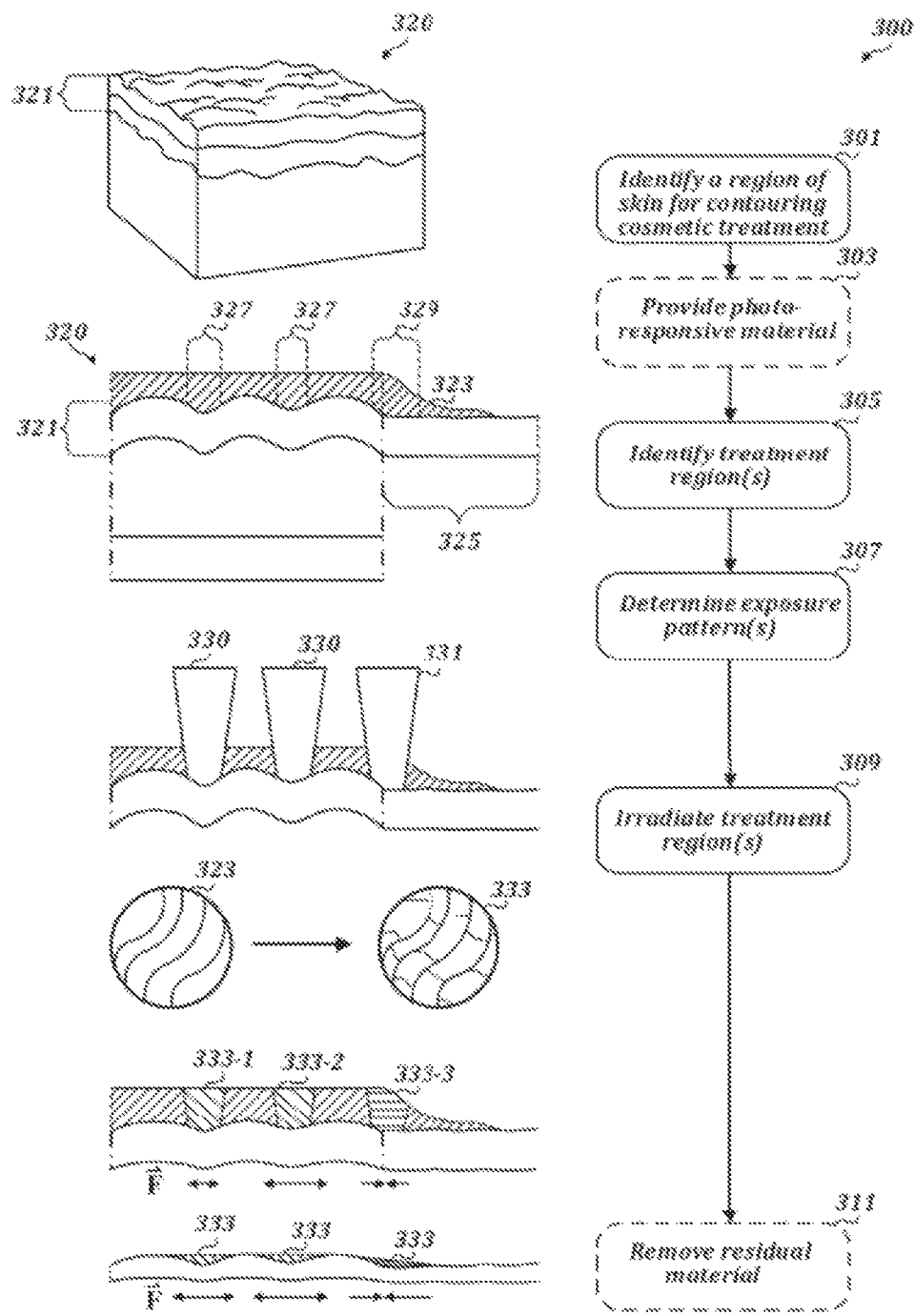
FIG. 3 is a schematic illustration of an example surface contouring treatment using photo-responsive materials, in accordance with various embodiments.

FIG. 3 is a schematic illustration of an example surface contouring treatment 300 using photo-responsive materials, in accordance with various embodiments. The individual operations of the example treatment 300 may be implemented by the system 100 of FIG. 1. As such, the example treatment 300 is described as part of an example flow implemented by a computer system and a computer-controlled illumination system (e.g., client computing device 104 of FIG. 1). In this way, the example treatment 300 may be stored as computer-executable instructions on a computer-readable memory that, when executed by one or more processors of the computer-controlled illumination system, may implement the operations of the flow illustrated in FIG. 3. It is understood that other systems and methods are contemplated, of which FIG. 3 describes but one example.

At operation 301, a region of skin 320 is identified as part of implementing a cosmetic treatment design. As described in more detail in reference to FIG. 2A-2B, a cosmetic treatment design may be or include a general cosmetic treatment based on a template. For example, aggregate data for images matched to a user's age, ethnicity, sex, or the like, may be used to identify and/or receive cosmetic treatment design templates, from which a system may include specific treatments based on facial mapping of the user. In some embodiments, by contrast, the example treatment 300 may begin directly with mapping the face of the user, rather than working from a template. Advantageously, initializing treatment with operation 301 directly, rather than modifying a template design, may facilitate spot treatments and may reduce the time and computational resources involved in applying surface contouring treatments. In some embodiments, the example surface contouring treatment 300 may include identifying multiple regions of skin including the region of skin 320. For example, treatment may include applying symmetric effects to opposing sides of a face (e.g., subject's face 102 of FIG. 1). In this way, the example cosmetic treatment 300 may include, at operation 301, identifying more than one region of skin to apply contouring treatments.

For surface treatments, contouring may be kept within the outer layers 321 of the skin 320, including but not limited to the epidermis, such that topical application of a photo-responsive material 323 may be used to apply the treatment, without involving subcutaneous injection or other invasive techniques. In this way, the example cosmetic treatment 300 may optionally include providing the photo-responsive material 323 to the surface of the skin 320 at operation 303. Providing may include applying the material manually or using other approaches, including but not limited to applying a mask, spray, or other application technique. The photo-responsive material 323 may be provided at the region of skin 320 and to areas around the region of skin 320, such as one or more peripheral regions 325 contiguous with or near the region of skin 320. In this context, the term "near" includes peripheral regions 325 that are not contiguous with the region of skin 320, but nonetheless are positioned such that contraction and/or expansion of the outer layers 321 of the skin 320 in the peripheral regions 325 affects the cosmetic treatment within the region of skin 320.

At operation 305, the example cosmetic treatment 300 includes identifying one or more treatment regions 327. The one or more treatment regions 327 may include a peripheral or anchoring treatment region 329, illustrated as extending from the region of skin 320 into the peripheral region 325. In the example treatment illustrated in FIG. 3, the treatments regions 327 and the peripheral treatment regions 329 are illustrated as a cosmetic treatment to smooth and/or contour lines or wrinkles in the outer layers 321 of the region of skin 320, illustrated in cross section. Other embodiments are contemplated, such as redistributing loose skin, tightening skin, reducing the appearance of scars, among other treatments currently addressed by surgical treatments or other interventions, such as botulinum toxin injections.

The treatment regions 327 correspond to one or more types of shape, morphology, and/or chemical modification of the photo-responsive material 323, as described in reference to FIG. 2A and FIG. 2B. For example, identification of the treatment regions 327 may include projecting a treatment design (e.g., treatment 200 of FIG. 2A) onto a mapping of a target body surface (e.g., projection 210 of FIG. 2B). Identification of the treatment regions 327 may also include detecting one or more features on the target body surface and modifying the treatment design onto a mapping of the target body surface. Still further, identification of the treatment regions 327 may include directly mapping the target body surface, classifying features detected on the target body surface, and identifying the treatment regions 327 using the classification. In an illustrative example, classification may include using a machine-learning model trained to classify images or other surface data (e.g., stereoscopic, multispectral and/or surface mapping data) into one or more of a number of possible feature classes. The training may include unsupervised learning processes, whereby the classifier is provided with a training set of images of the relevant modality, such that it optimizes an objective function (e.g., nearest neighbor, Euclidean distance, etc.) and is thereby configured to classify skin features with confidence. Additionally and/or alternatively, feature detection may be provided to the user via a display element (e.g., interface elements 110 of FIG. 1) to confirm and/or provide a classification of the feature. For example, the display may highlight features and, corresponding to the type of photo-responsive material 323 applied, may receive feedback from the user identifying the type of treatment to be applied to each respective feature.

At operation 307, the system determines an exposure pattern to effectuate the treatment at the treatment regions 327 and 329. As described in more detail in reference to FIG. 2B, the exposure pattern may be or include a tensor of exposure data describing one or more types of treatments surface, volumetric, aesthetic, etc.). In this way, the exposure pattern may include timing and spatial information for one or more photo-responsive materials. In the example of surface contouring treatment 300, the photo-responsive material 323 may be or include one or more constituent materials that expand when exposed to a first characteristic wavelength and contract when exposed to a second characteristic wavelength. Further, the expansion and contraction may be characterized by differing kinetic parameters (e.g., polymerization rate) and/or the treatment regions 327 may be of differing sizes, such that the exposure pattern may include spatial localization and timing information relating to one or more illumination sources (e.g., illumination sources 108 of FIG. 1). In this way, the expansion treatments may be effected by a first illumination source 330, while the contraction treatments may be effected by a second illumination source 331, according to the exposure patterns for each respective treatment region 327 of the region of skin 320. It is to be understood that example treatment 300 is not a limiting example. In some embodiments, contraction and expansion is applied in different manners, or may be applied alone. For example, more than two illumination sources may be applied, such that a treatment may include contraction, as well as other types of shape, morphology, or chemical change may be applied. The photo-responsive material 323, when cured, may adhere to the region of skin 320 and/or the peripheral region 325. Even so, after curing, the photo-responsive material 323 may remain soft and flexible.

At operation 309, the region of skin 320 is exposed to the first illumination source 330 and/or the second illumination source 331 at the treatment regions 327, as part of effecting the example treatment 300, As shown, the exposure may be such that the photo-responsive material 323 may undergo a chemical change, such as a photo-initiated polymerization or a cross-linking reaction to form a treated material 333. In some embodiments, the photo-responsive material 323 may be or include a hydrogel monomer that forms a crosslinked hydrogel in response to irradiation from the illumination sources 330 and/or 331. The hydrogel monomer may be or include, but is not limited to, gelatin methacryloyl (GelMA), hydroxyethylmethacrylate (HEMA), ethylene glycol diacrylate (EGDA). In some embodiments, the photo-responsive material 323 may also include a synthetic polymer. In some embodiments, the photo-responsive material 323 may include a stiffener, including, but not limited to calcium carbonate. In some embodiments, the photo-responsive material 323 may further include a photo-initiator. The photoinitiator may be characterized by two-photon absorption in the near-infrared (NIR) spectral range, defined from about 780 nm to about 900 nm, such that the illumination sources 330-331 may be or include NIR sources. The photoinitiator may be or include upconversion nanoparticles, including, but not limited to titanium oxide nanoparticles. The photoinitiator may be or include one or more water-soluble, biodegradable, and/or cytocompatible photoinitiators, such as 2,2'-Azobis[2-methyl-N-(2-hydroxyethyl)propionamide] (CAS Number: 61551-69-7), Lithium phenyl-2,4,6-trimethylbenzoylphosphinate (CAS Number 85073-19-4), or Eosin-Y. In some embodiments, the photoinitiator may be or include a combination of eosin Y, triethanolamine, and 1-vinyl-2-pyrrolidinone.

As illustrated, the change in morphology induced at operation 309 may differ between different treatment regions 327, corresponding to different illumination sources 330 being applied at different locations and/or for different exposure times. For example, a first treated material 333-1 may apply a different force ($\vec{F}$) to the outer layers 321 of the skin 320 than a second treated material 333-2, in terms of magnitude, direction, and/or type. For example, the first treated material 333-1 and the second treated material 333-2 may apply an expansion force, while a third treated material 333-3 (e.g., exposed to a different characteristic wavelength or a different illumination source) may apply a contraction force. Similarly, the magnitude of the forces applied by the first treated material 333-1 and the second treated material 333-2 may differ. In this way, exposure at operation 309 to irradiation from the illumination sources may induce different cosmetic treatments, at different positions, using the photo-responsive material 323. As such, the photo-responsive material may be applied uniformly to the region of skin 320, with the resulting treatment being modulated by the illumination sources 330.

Subsequent to exposing the photo-responsive material 323, the example treatment 300 may optionally include removing residual photo-responsive material 323 at operation 311. Removing residual material may also include removing excess treated material 333. The force applied to the region of skin 320 by the treated material may effect a visual reduction of the appearance of lines, wrinkles, loose skin, or other features, consistent with a contouring treatment. Where the photo-responsive material 323 is water-soluble, the treated material 333 may be water resistant. In this way, removal of residual material may include techniques available without specialized equipment or training, such as rinsing the region of skin 320.

Figure 4:
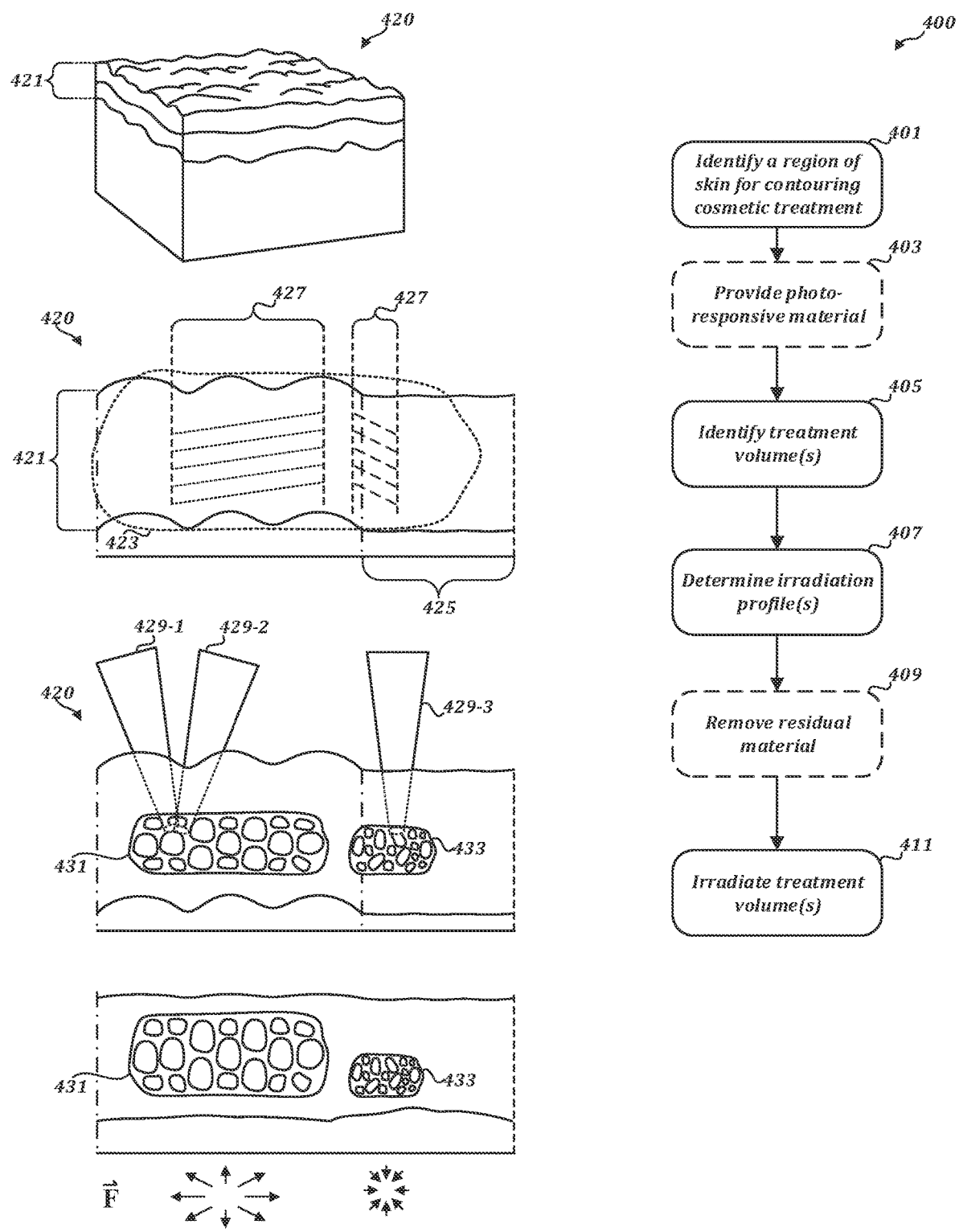
FIG. 4 is a schematic illustration of an example volumetric contouring treatment using photo-responsive materials, in accordance with various embodiments.

FIG. 4 is a schematic illustration of an example volumetric contouring treatment 400 using photo-responsive materials, in accordance with various embodiments. In contrast to the surface contouring treatments described in reference to FIG. 3, the example volumetric contouring treatment 400 illustrated in FIG. 4 includes forming a scaffold beneath the surface of a region of skin 420, such that the outer layers 421 of the region of skin 420 may be reshaped by modifying a photo-responsive material 423 that may be or include, but is not limited to, the photo-responsive materials described in reference to example surface contouring treatment 300 of FIG. 3. The individual operations of the example treatment 400 may be implemented by the system 100 of FIG. 1. As such, the example treatment 400 is described as part of an example flow implemented by a computer system and a computer-controlled illumination system (e.g., client computing device 104 of FIG. 1). In this way, the example treatment 400 may be stored as computer-executable instructions on a computer-readable memory that, when executed by one or more processors of the computer-controlled illumination system, may implement the operations of the flow illustrated in FIG. 4. It is understood that other systems and methods are contemplated, of which FIG. 4 describes but one example.

At operation 401, the example treatment 400 includes identifying the region of skin 420 on which to apply the volumetric contouring treatment. Volumetric contouring, in this context, may describe expansion and/or contraction of the outer layers 421 of the region of skin 420, for example, to reduce the visual appearance of wrinkles, lines, scars, loose skin, or thin skin. Identification of the region of skin 420 may include applications of digital image processing including, but not limited to, feature identification and tracking, vSLAM, edge-detection, keypoint detection, or the like. Additionally or alternatively, identification may include classification of features by trained machine-learning models, as described in more detail in reference to FIGS. 2A-3.

The example treatment 400 may optionally include providing the photo-responsive material 423 to the region of skin 420 and/or a peripheral region 425. Providing the photo-responsive material 423 may include applying the photo-responsive material 423 coextensive with the region of skin 420. As such, the example treatment 400 may include applying the photo-responsive material 423 over the entire target body surface (e.g., subject's face 102 of FIG. 1). For example, where the example treatment 400 is designed (e.g., treatment design 200 of FIG. 2A) to tighten loose skin around the eyes or to reduce the visual appearance of lines around the mouth, operation 403 may include applying the photo-responsive material 423 to the entire area around the eyes or the mouth, respectively. In this way, the entire region of skin 420 may be provided with photo-responsive material 423, as well as the peripheral region 425.

In some embodiments, the photo-responsive material 423 is absorbed at least partially into the outer layers 421 of the region of skin 420. In this way, the photo-responsive material 423 may be present beneath the surface of the region of skin 420, and may be targeted for shape or morphology modification as part of the example treatment 400. The photo-responsive material 423 may be or include a biocompatible and non-cytotoxic hydrogel monomer (e.g., GEL-MA) as described in reference to FIG. 3, Further, the photo-responsive material 423 may also include photo-initiator materials, such as upconversion nanoparticles, allowing the photo-responsive material 423 to be polymerized by a characteristic wavelength to which the outer layers 421 of the region of skin 420 and/or the peripheral region are transparent or translucent. For example, the characteristic wavelength may be or include wavelengths in the visible, near-infrared, or infrared energy ranges, where the outer layers 421 are at least partially transparent.

At operation 405, the example treatment 400 includes identifying treatment volumes 427, where one or more illumination sources (e.g., illumination sources 108 of FIG. 1) may be directed to the treatment volumes 427 to implement the example treatment 400. The treatment volumes 427 may be identified in reference to a treatment design that has been mapped onto the region of skin 420 (e.g., projection 210 of FIG. 2B), as described in more detail in reference to FIG. 2B, such that the treatment volumes 427 may overlap with the region of skin 420 and the peripheral region 425, respectively. The treatment volumes 427, may be or include regions internal to the outer layers 421 of the region of skin 420 and the peripheral region 425. The treatment volumes 427 may be differentiated, for example, by corresponding to different treatments, different illumination sources, different morphology changes, or the like. For example, as illustrated in FIG. 4, the treatment volume 427 internal to the region of skin 420, may correspond to an expansion treatment, while the treatment volume 427 at least partially internal to the peripheral region 425 may correspond to a contraction treatment. In this way, the combined effect of expansion and/or contraction treatments may be implemented at one or more treatment volumes 427 on a target body surface. In the illustrated example, the example treatment 400 fills loose skin in the region of skin 420, and tightens skin in the peripheral region 425. In this way, skin is spread and tightened in an approach that reduces the visible appearance of loose skin while also maintaining a natural aesthetic that is challenging for more invasive techniques, such as surgery or botulinum toxin injections.

At operation 407, the example treatment 400 includes determining irradiation profiles for the treatment volume(s) 427. As described in more detail in reference to FIG. 2A and FIG. 2B, the photo-responsive material 423 may be characterized by different dynamics for different types of transformations. For example, expansion may occur faster than contraction in response to exposure to illumination sources at the respective characteristic wavelengths. In this way, both characteristic wavelength, intensity, and exposure duration be determined as a function of position for the treatment volumes 427. In some embodiments, the irradiation profiles include depth information (e.g., positional dependency along a Z-axis, as opposed to a surface defined in two dimensions aligning with the surface of the region of skin 420), such that the irradiation profiles include graduated exposure three-dimensional space (e.g., volumetric exposure). In some embodiments, the irradiation profile is determined for isotropic expansion and/or contraction at the respective treatment volume 427. In some embodiments, the irradiation profiles may include patterning and/or meta-patterning information, such that the effect of exposure in accordance with the irradiation profile includes anisotropic expansion or contraction. In some embodiments, the irradiation profiles are determined such that portions of a particular treatment volume 427 expand, while other portions of the particular treatment volume 427 contract. In some embodiments, isotropic and/or anisotropic expansion or contraction permits different features to be addressed, such as fine lines, crow's feet, loose skin, cellulite, or the like, without surgical intervention or sub-cutaneous injection.

In some embodiments, the example treatment 400 optionally includes removing residual photo-responsive material 423 from the surface of the region of skin 420 and/or the peripheral region 425, at operation 409. Where illumination is targeted beneath the surface of the region of skin 420 and/or the peripheral region 425, differential absorption at the surface may affect or interfere with the intended treatment effect. In this way, removing the residual photo-responsive material 423 may improve the fidelity, efficacy, and/or performance of the example treatment 400. As the photo-responsive material 423 may be water-soluble (e.g., a hydrogel monomer), operation 409 may include removing by rinsing or absorbing the residual photo-responsive material 423 with an absorbent material.

At operation 411, one or more illumination sources 429 (e.g., illumination sources 108 of FIG. 1) may be applied to expose the photo-responsive material 423 in the treatment volumes 427, in accordance with the irradiation profiles. In some embodiments, three-dimensional exposure is effected by combining two or more focused beams. For example, a first illumination source 429-1 and a second illumination source 429-2 may be trained on the treatment volume 427, as an approach to control the fluence at a given point in the treatment volume 427 as a function of time. In this example, exposure control may be afforded by limiting the fluence of the first illumination source 429-1 and/or the second illumination source 429-2 below a threshold, above which the photo-responsive material 423 is activated and transforms into a first scaffold 431 (e.g., a crosslinked hydrogel). For example, through controlling the phases of the first illumination source 429-1 and the second illumination source 429-2 to provide constructive interference at the point of intersection, the net effect of the twin illumination sources is to activate the photo-responsive material 423 at precise positions described in the irradiation profile, in three-dimensions. While the illustration provided in FIG. 4 includes two illumination sources, it is understood that more than two illumination sources may be applied as part of the example treatment 400.

In some embodiments, dynamic optics may be implemented to provide three-dimensional control of exposure, in accordance with the irradiation profiles. For example, by adaptively focusing a third illumination source 429-3, a focal point may be modulated in three-dimensional space within the photo-responsive material 423, such that the energy density at the focal point activates the transformation into a second scaffold 433. The first illumination source 429-1, the second illumination source 429-2, and the third illumination source 429-3 may be generated by the same source, and may be characterized by the same central wavelength and fluence. In some cases, the third illumination source 429-3 may be characterized by a different set of parameters than the first illumination source 429-1 and the second illumination source 429-2. In this way, the first scaffold 431 may apply an expansion force ($\vec{F}$) to the outer layers 421 of the skin 420, while the second scaffold 433 may apply a contraction force to the outer layers 421 of the skin 420. The forces described in the context of the example treatment 400 are non-limiting, and it is understood that a combination of expansion and contraction forces may be applied to impart a net effect on the region of skin 420 as part of effecting the contouring treatment.

Figure 5:
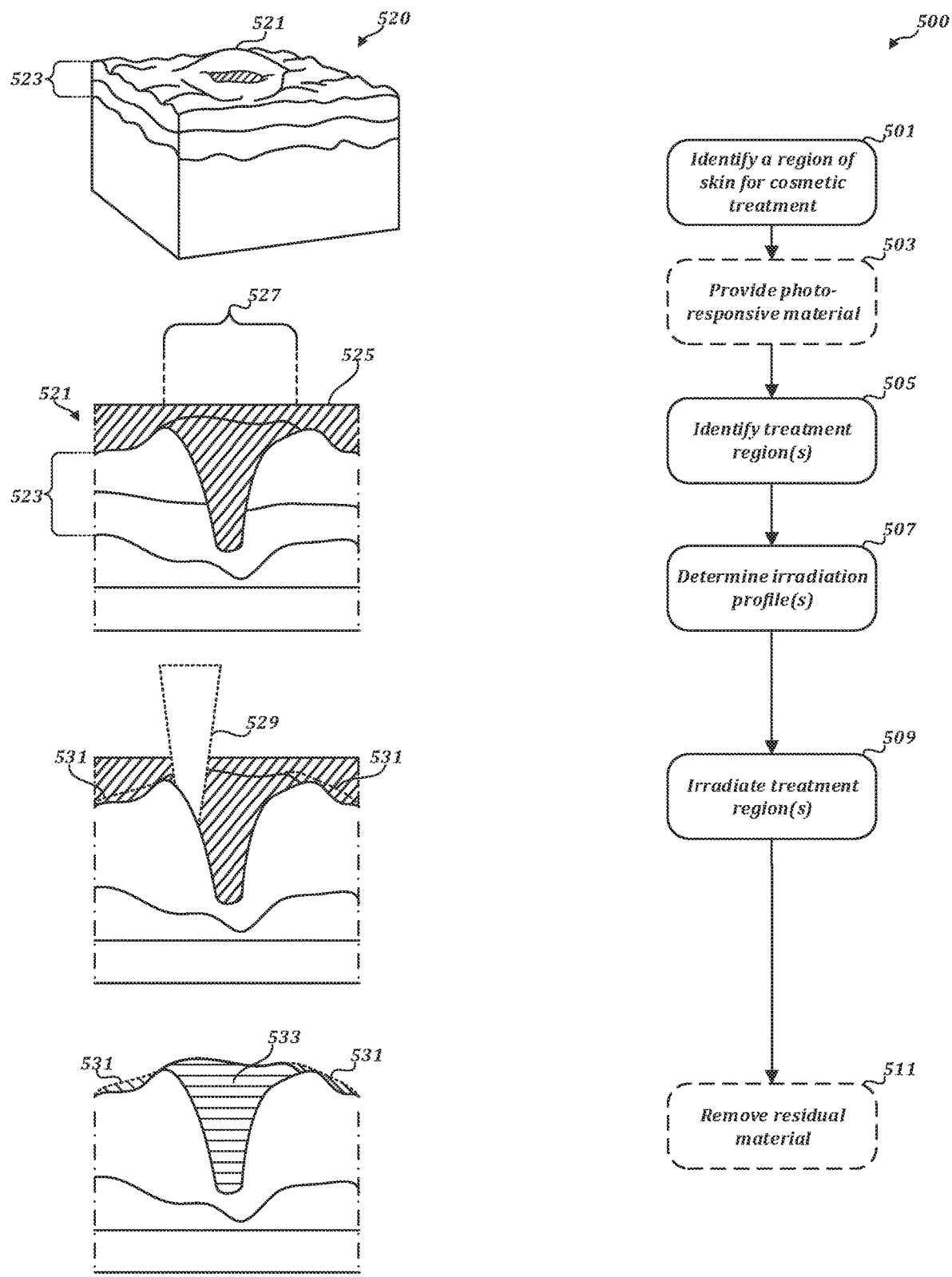
FIG. 5 is a schematic illustration of an example surface treatment for cosmetic contouring using photo-responsive materials, in accordance with various embodiments.

FIG. 5 is a schematic illustration of an example surface treatment 500 for cosmetic contouring using photo-responsive materials, in accordance with various embodiments. In some embodiments, the example surface treatment 500 includes identifying a region of skin 520 that expresses a feature 521 addressed by a particular cosmetic treatment, additionally and/or alternatively to the surface and volumetric treatments described in reference to FIGS. 3-4. The feature 521 may be or dude cosmetic or aesthetic aspects of the skin that are visible on the surface of the region of skin 520 and/or extend into the outer layers 523 of the region of skin. For example, the feature 521 may include, but is not limited to, acne scars, acne blemishes, moles, skin tags, warts, wart scars, biopsy scars, or other lines, scars, or blemishes. The individual operations of the example treatment 500 may be implemented by the system 100 of FIG. 1. As such, the example treatment 500 is described as part of an example flow implemented by a computer system and a computer-controlled illumination system (e.g., client computing device 104 of FIG. 1). In this way, the example treatment 500 may be stored as computer-executable instructions on a computer-readable memory that, when executed by one or more processors of the computer-controlled illumination system, may implement the operations of the flow illustrated in FIG. 5. It is understood that other systems and methods are contemplated, of which FIG. 5 describes but one example.

At operation 501, the region of skin 520 is identified, based on detection or recognition of the feature 521. As described in more detail in reference to FIG. 2A and FIG. 2B, the feature 521 may be detected by digital image processing of images collected by one or more image sensors (e.g., camera(s) 150 of FIG. 1). In some embodiments, the feature 521 is manually indicated by marking the feature 521 with an invisible indicator, such as a UV or IR absorbing ink. In this way, detection of the feature 521 may be automatic (e.g., without human intervention) where the example treatment 500 is implemented by an automated or partly automated system. Similarly, recognition by the system may follow indication of the feature 521 by a user of the system.

In some embodiments, the example treatment 500 may optionally include providing a photo-responsive material 525 to the region of skin 520 in the area of the feature 521, at operation 503. Where the feature 521 extends into the outer layers 523 of the region of skin 520, the photo-responsive material 525 may be applied to inner surfaces and/or volumes, for example, as illustrated in FIG. 5. The photo-responsive material 525 may be or include a biodegradable, water soluble, and/or non-cytotoxic material that is characterized by a transformation from a liquid or gel into a flexible and/or soft semi-solid material upon exposure to an illumination source at a characteristic wavelength. For example, the photo-responsive material may be or include a hydrogel monomer (e.g., GelMA) as described in reference to FIG. 3. The photo-responsive material 525 may include a pigment or a dye, selected to reduce the visual appearance of the feature 521 relative to the region of skin 520 surrounding it. The photo-responsive material 525 may include a suspension of metal or ceramic particles, acting as a dispersive medium when exposed to ambient conditions. In this way, the dispersive medium may cloak the inner surfaces of the feature 521 by partially reflecting ambient light from the surface of the photo-responsive material 525. The photo-responsive material 525 may be substantially transparent to photons having energy in the visible range from about 380 nm to about 750 nm. In this context, "substantially transparent" refers to an aesthetic evaluation of the photo-responsive material 525, such that a viewer would not observe the material under ambient conditions, rather than a quantitative measurement of absorption at any particular wavelength.

In some embodiments, the feature 521 may be associated with biological and/or physiological phenomena that benefit from sustained application of an active ingredient. For example, the feature 521 may be an acne blemish, a hive, an eczema blister, a wart, or other feature that includes an acidic bacterial or viral infection or otherwise causes discomfort. To that end, the photo-responsive material 525 may include an active ingredient to reduce the effect, duration, or discomfort of the feature 521, For example, where a hive or an eczema blister may present significant discomfort caused by itchiness, and may be aggravated by scratching, the photo-responsive material 525 may include an anti-pruritic compound. Similarly, where the feature 521 causes pain due to the presence of bacteria, photo-responsive material 525 may include an anesthetic and/or an antiseptic material. In such cases, the active ingredient may be soluble in the photo-responsive material 525 and stable under illumination at the characteristic wavelength(s) during the example treatment 500, such that the active ingredient may diffuse into the feature 521 over time, following the example treatment 500.

At operation 505, a treatment region 527 is identified corresponding to the feature 521. As described in more detail in reference to FIG. 2A and FIG. 2B, identifying the treatment region may include modifying a treatment design (e.g., treatment design 200 of FIG. 2A) with information describing the surface topography of the feature 521, as part of projecting the treatment design on to a mapping of the surface of the region of skin 520. In this way, a broader contouring treatment (e.g., example treatment 300 of FIG. 3 and/or example treatment 400 of FIG. 4) may be modified to include a targeted treatment of the feature 521. As described above in the context of recognition of the feature 521, a specific indicator material may be applied to facilitate the identification of the treatment region 527. In some embodiments, the indicator material and the photo-responsive material 525 are the same material. As such, depth measurements and mapping of the surface of the region of skin 520 may be used to refine the projection guiding the broader contouring treatments, and may apply a different treatment to the treatment region 527 than what may be applied to other regions on the target body surface (e.g., subject's face 102 of FIG. 1).

At operation 507, one or more irradiation profiles are determined, in accordance with the treatment design. Where the feature 521 includes internal volumes that extend into the outer layers 523 of the skin, the irradiation profiles may include surface treatment information and volumetric treatment information, as described in reference to FIG. 2B, to induce different transformations on the outer surface(s) of the feature 521 relative to the internal surface(s) of the feature 521. In the illustration provided in FIG. 5, the treatment region 527 describes the inner volume of the feature 521, but the irradiation profile may also include the surfaces of the feature 521 external to the treatment region 527. In this way, different cosmetic and/or aesthetic effects may be imparted to the different surfaces of the feature 521. As described in more detail in reference to FIG. 3 and FIG. 4, the irradiation profiles may be or include tensors of wavelength, intensity, and/or duration information for one or more illumination sources 529 to effect the example treatment 500.

At operation 509, the illumination source 529 provides energy at the characteristic wavelength such that the photo-responsive material 525 is transformed into a first semi-solid material 531 external to the feature 521 and/or a second semi-solid material 533 internal, coextensive, and/or overlying the feature 521. In some embodiments, the example treatment 500 may generate the second semi-solid material 533, such that the second semi-solid material 533 acts as an edge-diffuser and/or a background diffuser of visible wavelengths. For example, the second semi-solid material 533 may define a convex surface at or near the surface of the feature 521. In this way, the surfaces of the feature 521 may collect light and may appear lighter. In some embodiments, photo-responsive material is cross-linked by exposure to the illumination source 529 to form a cross-linked hydrogel that applies an isotropic or anisotropic force to the feature 521. In this way, the second semi-solid material 533 may shrink the physical size of the feature 521, for example, by contracting the internal volume of the feature 521, or by expanding the feature and thereby reducing its visual prominence. In some embodiments, the first semi-solid material 531 is characterized by different optical properties from the second semi-solid material 533. For example, while the second semi-solid material 533 may be an edge and/or background diffuser, the first semi-solid material may be a diffuse reflector, for example, by inclusion of a dye or pigment that concentrates under contraction of the first semi-solid material 531. At operation 511 residual or excess material 531 may be removed.

Figure 6A:
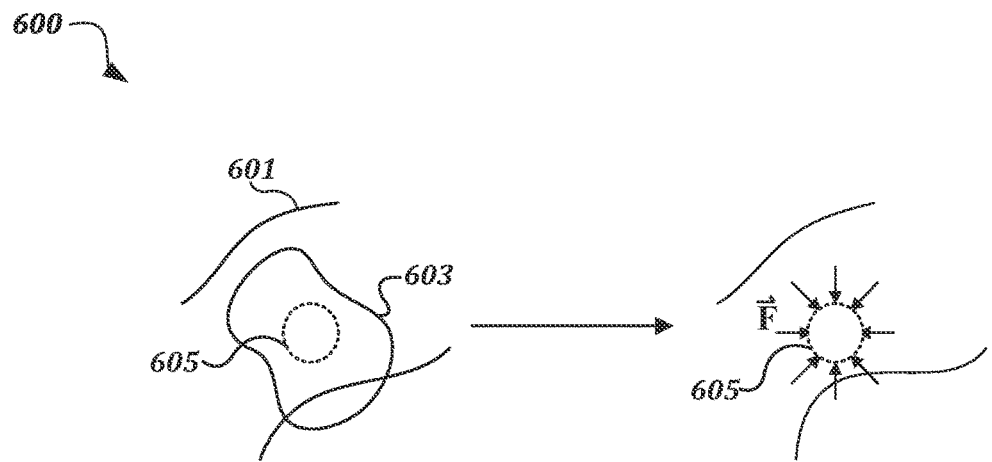
FIG. 6A is a schematic illustration of an example isotropic contouring treatment, in accordance with various embodiments.
Figure 6B:
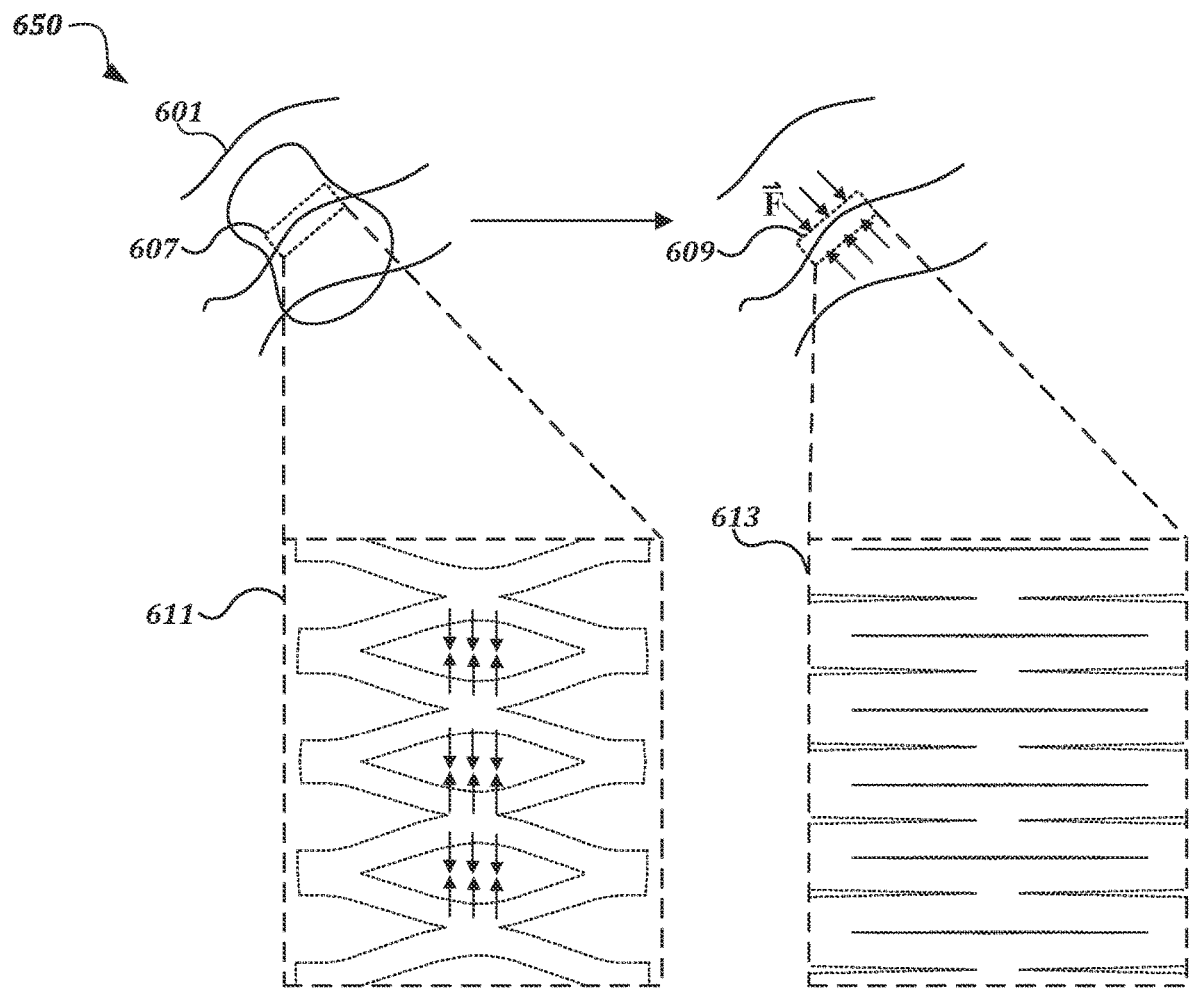
FIG. 6B is a schematic illustration of an example anisotropic contouring treatment, in accordance with various embodiments.

FIGS. 6A-6B describe isotropic and anisotropic contouring applied as part of a contouring treatment, through patterned exposure of photo-responsive materials as defined by irradiation profiles, as described in more detail in reference to FIGS. 2-5. While the description focuses on surface treatments, as described in reference to FIG. 3, it is understood that patterning is also contemplated in three-dimensional irradiation profiles in the context of volumetric contouring treatment, as described in reference to FIG. 4.

FIG. 6A is a schematic illustration of an example isotropic contouring treatment 600, in accordance with various embodiments. As part of applying a contouring treatment, a region of skin 601 (e.g., region of skin 320 of FIG. 3) may be provided with one or more photo-responsive materials 603 (e.g., photo-responsive material 323 of FIG. 3, photo-responsive material 423 of FIG. 4, or photo-responsive material 525 of FIG. 5). The photo-responsive material 603 may be coextensive with the region of skin 601, or may at least partially overlie the region of skin 601. A treatment region 605 (e.g., treatment region 327 of FIG. 3) may be defined as substantially symmetrical, for example, ellipsoidal, circular, or oblong. Following exposure to an illumination source (e.g., illumination source 108 of FIG. 1), the photo-responsive material 603 may polymerize or otherwise change shape, such that an isotropic force ( $\vec{F}$ ) is applied to the region of skin 601. The force may be isotropic contraction or expansion, as defined by the irradiation profile for the example isotropic contouring treatment 600. As illustrated, isotropic contraction force may be suitable for tightening loose skin, for reducing the appearance of surface features, or other cosmetic contouring. In some cases, isotropic force may be applied at small scale, for example, by focusing the illumination source down to a point. Through control of the spot size and the location of the exposure, the treatment region 605 can be sized to impart the isotropic force on multiple scales. For example, a large spot size may impart isotropic contraction on a region of a user's face, while a small spot size may be applied to regions of skin 601 that are feature-dense, such as around the eyes and/or mouth. In an illustrative example, the illumination source may be or include a laser source, such that the spot size is on the order of micrometers to millimeters. As such, a treatment region defining a circular area of the region of skin 601 with a diameter of 1 cm may be defined by rastering and/or scanning the laser over the region of skin 601. In another example, the illumination source may be a projector or other wide-beam source (e.g., a lamp) that is reflected or transmitted via an addressable array of filters forming a pixel map. As such, the minimum size of the treatment region 605 is the size of a single pixel, as transformed by projection optics onto the surface of the region of skin 601. In this way, the shape of the treatment region 605 may be exposed by scanning and/or rastering a small spot size (e.g., a marrow beam source) or by projecting an image onto the region of skin 601.

FIG. 6B is a schematic illustration of an example anisotropic contouring treatment 650, in accordance with various embodiments. Advantageously, scanning and/or rastering a beam, or projecting an image, as described in reference to FIG. 6A, provides the capability to form a patterned treatment region 607, such that an anisotropic force 609 is applied upon exposure to the illumination source. While it is also possible to pattern the photo-responsive material 603, for example, through use of a stencil, resolution and complexity of patterning is improved through patterned exposure (e.g., as when exposure is computer-controlled). In an illustrative example, the region of skin 601 includes loose skin that expresses parallel lines or wrinkles. As such, a pattern 611 may be defined such that, when the photo-responsive material 603 is exposed to an illumination source that induces a shape change 613, an anisotropic contraction force is applied. The pattern 611 is intended as an illustrative example, and it is understood that other patterns are contemplated. In some embodiments, patterns 611 may combine expansion and contraction of the photo-responsive material 603 as an approach to forming net forces that are spatially dependent, and may be addressed to regions of skin that include multiple features or may otherwise benefit from more than one contouring treatment. Also advantageously, anisotropic force application may permit areas of the region of skin 601 to be anchored in place, permitting isotropic treatments applied elsewhere in the region of skin 601 to apply a desired aesthetic effect. As an illustrative example, anchoring skin near the temples of the face may permit isotropic contraction nearer the eyes to impart an appearance of lifting the skin on the face toward the temples. Similarly, patterning photo- the responsive materials 603 beneath the surface of the region of skin 601 may permit non-uniformity in the skin surface to be treated with precision, rather than by distribution of isotropic force. For example, anisotropic contraction may be applied to form dimples or isotropic expansion may be applied to reduce the appearance of dimples (e.g., in cases of severe cellulite).

Through precise control of exposure according to irradiation profiles defined with detailed mappings of target body surfaces, the example isotropic contouring treatment 600 and the example anisotropic contouring treatment 650 may be applied, alone or in combination, to provide a contouring treatment to a target body surface. In some embodiments, precision and accuracy are provided by automated treatment systems (e.g., client computing device 104 of FIG. 1), configured to implement the example treatments described above in reference to FIGS. 3-6B.

Figure 7:
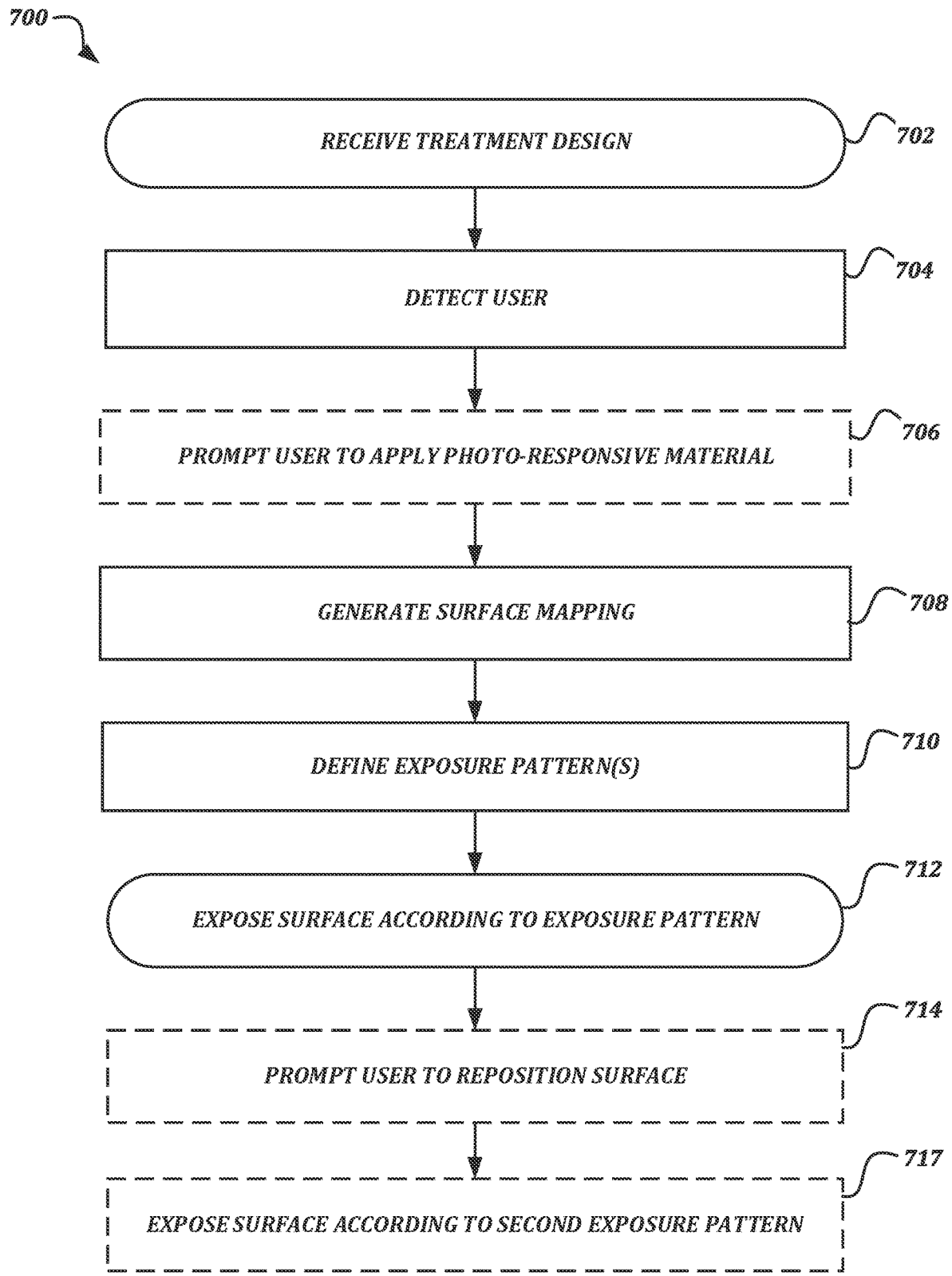
FIG. 7 is a flowchart that illustrates an example method for applying a contouring treatment, in accordance with various embodiments.

FIG. 7 is a flowchart that illustrates an example method 700 for applying a contouring treatment, in accordance with various embodiments. The example method 700 may be performed by a computer system including one or more computing devices, such as client computing device 104 of FIG. 1, The example method 700 may be stored as computer-executable instructions on a computer-readable memory device. In this way, the computer system may implement the operations of example method 700 as part of executing the instructions.

At operation 702, the computer system receives a numerical representation of a cosmetic contouring treatment design. The numerical representation of the contouring treatment design includes a tensor of contouring information for one or more photo-responsive materials. The photo-responsive materials correspond to a contouring formulation (e.g., photo-responsive material 323 of FIG. 3, photo-responsive material 423 of FIG. 4, or photo-responsive material 525 of FIG. 5) including a mixture of water-soluble, biodegradable, non-cytotoxic components that change shape, expand, and/or contract when exposed to an illumination source at a characteristic wavelength. The computer system may receive the numerical representation of the contouring treatment (e.g., contouring treatment 200 of FIG. 2) from a user through a user interface of the computer system or through a personal electronic device. The numerical representation of the contouring treatment may be associated with a unique design identifier and may be retrieved from a data store, such that the tensor of contouring information may be requested and/or retrieved by the computer system in response to receiving the unique design identifier.

At operation 704, the computer system detects, using a camera in electronic communication with the computer system, a user of the system facing a visible light mirror (e.g., mirror 106 of FIG. 1). In some embodiments, the camera is in optical communication with the visible light mirror via a partially transparent portion of the visible light mirror (e.g., first portion 112-1 of FIG. 1). In this context, detecting the user may include multiple operations included as part of face-detection and recognition routines. For example, the computer system may store feature data for a number of faces, such that the computer system is able to detect and identify the face present in the field of view of the camera (e.g., field of view 152 of FIG. 1). Such identification may benefit the system by reducing the resource demand associated with generating face mappings and projections. For example, by storing depth and image data, the computer system may rely on periodic re-initialization for 3D mapping operations, rather than continuous mapping, which may be more computationally intensive.

The method 700 may optionally include generating, by the computer system, a prompt for the user to apply the mixture of photo-responsive materials at operation 706. As described in reference to FIG. 1, prompting the user to apply the photo-responsive materials may serve as one of a number of visual/auditory guides or prompts provided to the user. Such prompts may facilitate the application of contouring treatment, for example, where the client computing device is not equipped with a sensor to detect the presence of the photo-responsive material. In some embodiments, the photo-responsive material includes a constituent compound or that is detectable optically. For example, the photo-responsive material may include a compound that absorbs a characteristic wavelength for which the computer system is provided with a source that is typically reflected by human skin. Additionally and/or alternatively, the matrix may include a material that reflects or fluoresces under a characteristic wavelength of illumination. In this way, the optional operation 706 may be triggered in response to the computer system determining that the user has not applied the photo-responsive material.

At operation 708, the computer system generates, using the camera, a numerical representation of a portion of a target body surface of the user (e.g., region of interest 120 of subject's face 102 of FIG. 1). The numerical representation of the target body surface includes a tensor of position information defining the surface. The tensor of position information is described in other terms as a face-mapping or a 3D mapping. The computer system may implement various techniques to collect and generate depth data describing the surface to which the contouring treatment will be applied. For example, the computer system may incorporate or be electronically coupled with sensors including, but not limited to, time-of-flight cameras, stereoscopic cameras, LiDAR sensors, or point-tracking systems, to generate the numerical representation of the target body surface. As described in more detail in reference to FIG. 1 the numerical representation of the surface may be stored in memory of the computer system and/or in a separate data store for use in generating projections of the cosmetic design onto the 3D mapping.

At operation 710, the computer system defines one or more exposure patterns for the surface, at least in part by projecting the tensor of contouring information onto the tensor of position information. As described in more detail in reference to FIGS. 2-6B, the exposure patterns may include data for a set of characteristic wavelengths generated by the illumination sources incorporated or in electronic communication with the computer system. For example, an exposure pattern may include spatially localized emission levels and durations for each cell in a map of polygons (e.g., polygons 212 of FIG. 2B) corresponding to a position on the face.

In this way, the computer system a generate an exposure sequence, in terms of drive instructions for the sources, to apply the cosmetic design to the specific surface of the user.

At operation 712, using an illumination source (e.g., illumination source 108 of FIG. 1) in electronic communication with the computer system, the computer system exposes a portion of the user's skin (e.g., region of interest 120 of FIG. 1) with one or more discrete wavelength channels. The exposure is effected in accordance with the exposure pattern. In some embodiments, the illumination source is physically coupled with the visible light mirror and configured to emit the discrete wavelength channels. In some embodiments, the illumination source is optically coupled with the mirror via a unidirectional transparent portion (e.g., second portion 112-2 of FIG. 1), such that the illumination source emits the plurality of discrete wavelength channels through the mirror via the unidirectional transparent portion. The sources can be steered by the computer system as part of processing the exposure pattern into drive instructions for the sources. For example, the sources may include beam steering optics that rely on electronic actuation or dynamic lensing/optics to direct the source beam toward a specific position on a user's face. In some embodiments, the sources are configured to emit a field of light covering the entire surface, but with variable wavelength content at each of a number of pixels, reproducing the projected design, as described in more detail in reference to FIG. 2B. In such cases, the sources may include dynamic filters, such as programmable diffraction grating arrays or programmable filter arrays, as in digital light projection.

The method 700 may optionally include operation 714, whereby the computer system generates a second prompt for the user to reposition relative to the cameras (e.g., reposition from a face-on posture to a semi-profile posture), such that the illumination sources may be aligned with a different portion of the face. Multiple angles of exposure may permit the system to form more precise patterns or to control exposure in feature-dense regions of skin. Subsequent operation 714, the method 700 may optionally include operation 717, whereby the computer system exposes the target body surface according to a second exposure pattern. The second exposure pattern may include low-angle illumination, as part of applying surface exposure without penetrating into the outer layers of skin (e.g., outer layers 321 of FIG. 3). In this way, surface contouring and volumetric contouring may be applied in a single treatment session, with a single application of photo-responsive material. Similarly, operation 717 may include face-on illumination of a second portion of the target body surface, such that a different region may express a different contouring effect according to the contouring treatment design received at operation 702.

Figure 8:
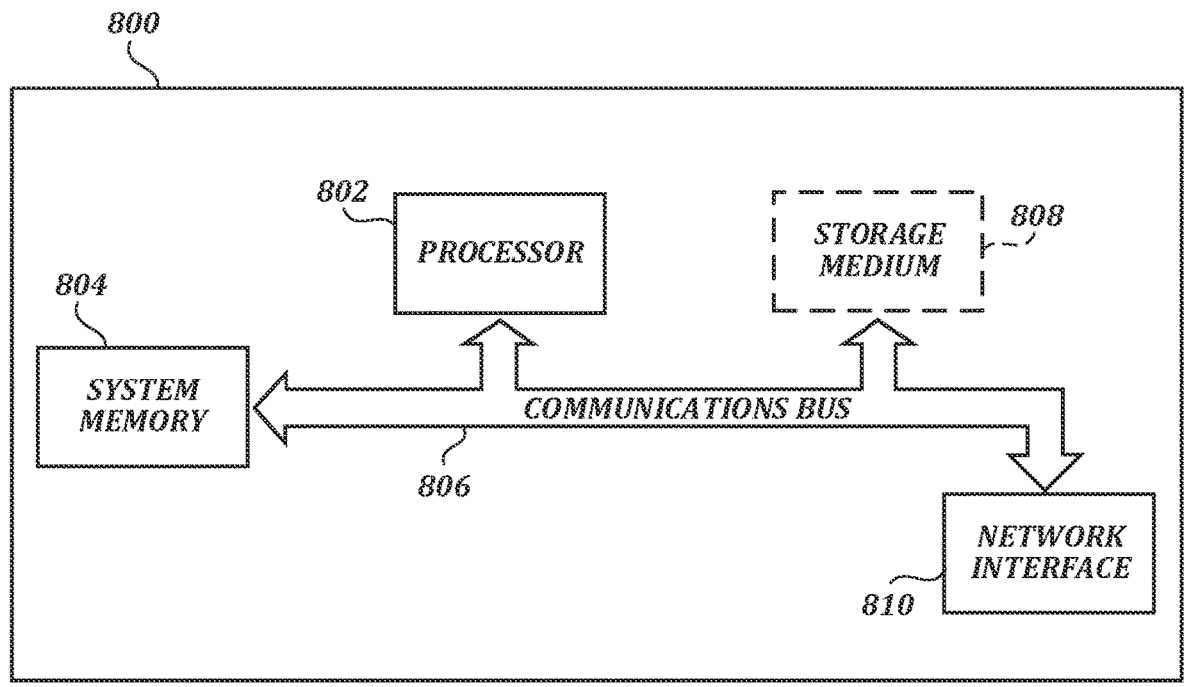
FIG. 8 is a block diagram that illustrates aspects of an illustrative computing device appropriate for use as a computing device of the present disclosure.

FIG. 8 is a block diagram that illustrates aspects of an example computing device 800, in accordance with various embodiments. The exemplary computing device 800 describes various elements that are common to many different types of computing devices. While FIG. 8 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 800 may be any one of any number of currently available or yet to be developed devices.

In its most basic configuration, the computing device 800 includes at least one processor 802 and a system memory 804 connected by a communication bus 806. Depending on the exact configuration and type of device, the system memory 804 may be volatile or nonvolatile memory, such as read only memory ("ROM"), random access memory ("RAM"), EEPROM, flash memory, or similar memory technology. Those of ordinary skill in the art and others will recognize that system memory 804 typically stores data and/or program modules that are immediately accessible to and/or currently being operated on by the processor 802. In this regard, the processor 802 may serve as a computational center of the computing device 800 by supporting the execution of instructions.

As further illustrated in FIG. 8, the computing device 800 may include a network interface 810 comprising one or more components for communicating with other devices over a network. Embodiments of the present disclosure may access basic services that utilize the network interface 810 to perform communications using common network protocols. The network interface 810 may also include a wireless network interface configured to communicate via one or more wireless communication protocols, such as Wifi, 2G, 3G, LTE, WiMAX, Bluetooth, Bluetooth low energy, and/or the like. As will be appreciated by one of ordinary skill in the art, the network interface 810 illustrated FIG. 8 may represent one or more wireless interfaces or physical communication interfaces described and illustrated above with respect to particular components of the system 100.

In the exemplary embodiment depicted in FIG. 8, the computing device 800 also includes a storage medium 808. However, services may be accessed using a computing device that does not include means for persisting data to a local storage medium. Therefore, the storage medium 808 depicted in FIG. 8 is represented with a dashed line to indicate that the storage medium 808 is optional. In any event, the storage medium 808 may be volatile or nonvolatile, removable or nonremovable, implemented using any technology capable of storing information including, but not limited to, a hard disk drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 804 and storage medium 808 depicted in FIG. 8 are merely examples of computer-readable media.

Suitable implementations of computing devices that include a processor 802, system memory 804, communication bus 806, storage medium 808, and network interface 810 are known and commercially available. For ease of illustration and because it is not important for an understanding of the claimed subject matter, FIG. 8 does not show some of the typical components of many computing devices. In this regard, the computing device 800 may include input devices, such as a keyboard, keypad, mouse, microphone, touch input device, touch screen, and/or the like. Such input devices may be coupled to the computing device 800 by wired or wireless connections including RF, infrared, serial, parallel, Bluetooth, Bluetooth low energy, USB, or other suitable connections protocols using wireless or physical connections. Similarly, the computing device 800 may also include output devices such as a display, speakers, printer, etc, Since these devices are well known in the art, they are not illustrated or described further herein.

While illustrative embodiments have been illustrated and described, it will be appreciated that various changes can be made therein without departing from the spirit scope of the devices, methods, and systems described.

The invention claimed is:

1. A method of contouring skin, the method comprising:
   identifying a region of skin corresponding to a contouring treatment of the skin;
   providing the region of skin with a photo-responsive material, the photo-responsive material overlying a portion of the region of the skin;
   identifying one or more treatment regions overlapping the photo-responsive material, the treatment regions being identified at least in part to apply the contouring treatment; thereafter
   determining a three-dimensional irradiation profile for each of the one or more treatment regions to contour each respective treatment region as part of applying the contouring treatment; and
   irradiating with two or more focused beams, at a plurality of select locations, the photo-responsive material at the one or more treatment regions in accordance with the respective irradiation profiles, wherein irradiating the photo-responsive material at the plurality of select locations with the two or more focused beams providing constructive interference at a point of intersection, thereby inducing a localized change in shape of the photo-responsive material in the respective treatment regions, and wherein the photo-responsive material comprises a hydrogel monomer that forms a cross-linked hydrogel when under illumination at a characteristic wavelength.

2. The method of claim 1, wherein said localized change in shape of the photo-responsive material in the respective treatment regions from irradiating the photo-responsive material defines one or more of contraction or expansion of one or more outer layers of the region of skin, wherein the region of skin is coextensive with lines or wrinkles of the skin, and wherein the contouring treatment comprises expanding or contracting the skin within or around the region of skin.

3. The method of claim 1, wherein the irradiation profile defines a volumetric pattern within the treatment region, and wherein the localized change in shape caused by irradiating the photo-responsive material in accordance with the respective irradiation profiles defines a contraction or an expansion of one or more outer layers of the region of skin.

4. The method of claim 1, wherein the photo-responsive material is characterized by a physical contraction in response to illumination at a characteristic wavelength.

5. The method of claim 1, wherein the photo-responsive material is characterized by a physical expansion in response to illumination at a characteristic wavelength.

6. The method of claim 1, wherein the photo-responsive material comprises first and second constituent materials, and wherein:
   the first constituent material of the first and second constituent materials expands in a manner characterized by a first kinetic parameter in response to exposure at a first characteristic wavelength; and
   the second constituent material of the first and second constituent materials contracts in a manner characterized by a second kinetic parameter in response to exposure at a second characteristic wavelength.

7. The method of claim 1, wherein the hydrogel monomer comprises gelatin methacryloyl (Gel-MA), hydroxyethylmethacrylate (HEMA), or ethylene glycol diacrylate (EGDA).

8. The method of claim 1, wherein:
the irradiation profile for a treatment region of the one or more treatment regions defines a pattern that induces an anisotropic contraction or an anisotropic expansion of an area of the region of skin.

9. The method of claim 1, wherein identifying the region of skin comprises:
capturing, by a camera, one or more images of the region of skin; and
determining a feature of the skin based on the one or more images.

10. The method of claim 9, wherein determining the feature of the skin comprises:
generating a 3D mapping of the skin; and
predicting a location and a type of the feature of the skin on the 3D map using a feature detection system configured to recognize the feature of the skin when provided with the 3D map of the skin.

11. The method of claim 10, further comprising:
receiving a numerical representation of a contouring treatment design; and
modifying the contouring treatment design to reflect the location and the type of the feature of the skin.

12. The method of claim 9, wherein the feature of the skin includes a wrinkle, a fine line, a scar, a blemish, or a region of loose skin.

13. A non-transitory computer-readable memory storing instructions that, when executed by one or more processors of a computer system, cause the system to implement operations of the method of claim 1.

14. The method of claim 1, wherein the photo-responsive material is either pigmented or not pigmented, the method further comprising
removing residual photo-responsive material.

15. The method of claim 1, wherein the irradiation has two or more characteristics selected from the group consisting of irradiation wavelength, duration and intensity, wherein the irradiation characteristics for at least two select locations of the plurality of select locations differ with respect to the other in irradiation wavelength, duration or intensity.

16. A method of contouring skin, the method comprising:
identifying a region of skin corresponding to a contouring treatment of the skin;
applying a composition having at least one photo-responsive material over the region of skin;
identifying a treatment region associated with the photo-responsive material;
determining an irradiation profile for the treatment region to contour the treatment region as part of applying the contouring treatment, the irradiation profile including a characteristic wavelength, an intensity and a duration for first and second specific locations associated with the first treatment region, wherein the irradiation profile is configured so that at least one of the characteristic wavelength, the intensity and the duration for the first specific location is different from at least one of the characteristic wavelength, the intensity and the duration for the second specific location; and
irradiating the composition having the at least one photo-responsive material at the two or more specific locations associated with the first treatment region in accordance with the respective irradiation profile, wherein irradiating the photo-responsive material induces a localized change in shape of the photo-responsive material in the treatment region.

17. The method of claim 16, wherein the composition includes two photo-responsive materials, each of the photo-responsive materials contracts or expands in response to illumination at a characteristic wavelength.

18. The method of claim 17, wherein one of the two photo-responsive materials contracts in response to illumination at a characteristic wavelength and the other one of the two photo-responsive materials expands in response to illumination at a characteristic wavelength.

19. The method of claim 16, wherein the a least one photo-responsive material comprises a first photo-responsive material and a second photo-responsive material, the first photo-responsive material configured to expand in response to exposure of the irradiation, and the second photo-responsive material configured to contract in response to exposure to the irradiation.

20. A method of contouring skin, the method comprising:
selecting a tensor of contouring information from a computer system;
identifying a region of skin corresponding to a contouring treatment of the skin;
detecting with a camera the region of skin corresponding to the contouring treatment of the skin;
generating with the computer system a tensor of position information defining the region of skin;
providing the region of skin with a composition having at least one photo-responsive material, wherein the at least one photo-responsive material is configured to induce a localized change in shape of the photo-responsive material from exposure to irradiation, the composition overlying a portion of the region of the skin and defining a composition coverage area;
identifying a treatment region overlapping the composition coverage area, the treatment regions being identified at least in part to apply the contouring treatment; thereafter
determining an irradiation profile for the treatment region to contour the treatment region as part of applying the contouring treatment, wherein the irradiation profile is defined by information comprising the tensor of contouring information projected onto the tensor of position information; and
in accordance with the irradiation profile, solely irradiating a plurality of select locations of the composition coverage area associated with the treatment region, wherein the photo-responsive material comprises a hydrogel monomer that forms a crosslinked hydrogel when under illumination at a characteristic wavelength.

* * * * *